(12) United States Patent
Birkbeck et al.

(10) Patent No.: US 7,129,204 B2
(45) Date of Patent: Oct. 31, 2006

(54) PERFUMES

(75) Inventors: Anthony Alexander Birkbeck, Kent (GB); Olivier Moulin, Kent (GB); Christine Nagel, Neuilly sur Seine (FR); Keith Douglas Perring, Kent (GB); Charles Stanley Sell, Kent (GB); Kathleen Mary Tuck, Kent (GB)

(73) Assignee: Quest International Services B.V., Naarden (NL)

( * ) Notice: Subject to any disclaimer, the term of this patent is extended or adjusted under 35 U.S.C. 154(b) by 344 days.

(21) Appl. No.: 10/296,805

(22) PCT Filed: Jun. 1, 2001

(86) PCT No.: PCT/GB01/02446

§ 371 (c)(1),
(2), (4) Date: May 12, 2003

(87) PCT Pub. No.: WO01/93823

PCT Pub. Date: Dec. 13, 2001

(65) Prior Publication Data

US 2003/0199422 A1    Oct. 23, 2003

(30) Foreign Application Priority Data

Jun. 2, 2000    (EP) ................................ 00304721

(51) Int. Cl.
*C11B 9/00* (2006.01)

(52) U.S. Cl. ........................................................ 512/2

(58) Field of Classification Search ................. 512/2
See application file for complete search history.

(56) References Cited

U.S. PATENT DOCUMENTS

| 3,330,730 A | 7/1967 | Hernandez .................. 167/85 |
| 4,511,495 A | 4/1985 | Melville ...................... 252/522 |
| 5,500,138 A | 3/1996 | Bacon et al. ................. 252/8.6 |
| 6,413,920 B1 * | 7/2002 | Bettiol et al. ................ 510/101 |
| 6,858,575 B1 * | 2/2005 | Smets et al. .................... 512/2 |

FOREIGN PATENT DOCUMENTS

| DE | 1 492 322 | 1/1970 |
| EP | 0 971 024 A1 | 1/2000 |

(Continued)

OTHER PUBLICATIONS

Arctander S.: "Perfume and Flavor Chemicals (Aroma Chemicals)", Monclair, US XP002174800 01896 examples 26, 2514, 3070, date?.

*Primary Examiner*—Monique T. Cole
(74) *Attorney, Agent, or Firm*—Morgan Lewis & Bockius LLP

(57) ABSTRACT

A substantially odorless aromatic amine trapping agent is used in a composition including perfume for the purpose of enabling the perfume and trapping agent to react chemically together spontaneously and reversibly to form a reaction product form which the perfume can be released. In the reaction product, the perfume may be protected against degradation, premature evaporation etc., with the perfume being releasable from the reaction product. In contrast to a pro-perfume, the reaction product formed the present invention is not used by being included as such in a mixture of perfumes or perfumed product, but instead the perfume and trapping agent are included in a mixture of perfumes or perfumed product where they react spontaneously in situ to form a transient reaction product for subsequent release of the perfume. The invention also provides a perfume composition including the trapping agent.

9 Claims, 3 Drawing Sheets

FOREIGN PATENT DOCUMENTS

| | | |
|---|---|---|
| EP | 0 971 025 A1 | 1/2000 |
| EP | 1 004 654 A2 | 3/2000 |
| WO | 99/46318 | 9/1999 |

* cited by examiner

PERFUMES

FIELD OF THE INVENTION

This invention concerns perfumes. In this specification the term "perfume" is used to mean a fragrant chemical substance which exhibits odour properties, ie has a generally discernible odour or smell under normal ambient conditions of pressure (atmospheric) and temperature (about 20° C.), the odour usually generally being regarded as pleasant or attractive, or at least inoffensive, but possibly being unpleasant in nature.

BACKGROUND TO THE INVENTION

A large number of perfumes are known and are widely used in consumer products (referred to herein as "perfumed products"), typically to impart a desired odour to the product itself or to a substrate following use of the product, eg on skin following use of a fine fragrance product, perfumed soap etc, on clothes following use of a perfumed laundry product etc. Perfumes are usually used by being formulated into mixtures of perfumes, often containing a large number of different perfumes, to produce a mixture having desired odour properties, typically mixed with or dissolved in a suitable solvent or mixed with a solid substrate.

It is known that certain perfumes are liable to suffer from reduced efficacy over time on storage in a perfumed product. This can be due to loss of volatile fragrant materials, such as volatile aldehydes and alcohols, or due to degradation, eg as a result of chemical reaction with other materials such as bleach in the product, with oxygen in ambient air etc. Some perfumes are also chemically unstable in use and so do not function to impart odour properties for as long as desirable: for example, aldehydes can be subject to oxidation on exposure to air.

In an attempt to overcome such problems, so-called "pro-perfumes" or "pro-fragrances" have been devised. These generally comprise a derivative of a perfume that is more stable than the perfume itself, eg being less volatile, being chemically protected from taking part in undesired reactions etc, and from which the perfume can be released in use, eg in response to water (hydrolysis), heat (thermolysis) etc. The pro-perfume is included in a mixture of perfumes or a perfumed product in place of the perfume. See, for example, WO 99/46318 which concerns various silicone polymer pro-fragrances.

WO 00/02981 discloses laundry and cleaning compositions including a product of reaction between a primary and/or secondary amine compound e.g. ethyl 4-aminobenzoate (having an Odour Intensity Index of less than that of a 1% solution of methylanthranilate in dipropylene glycol) and a perfume component selected from ketone, aldehyde and mixtures thereof, the reaction product generally being an azomethine (also known as a Schiff's base or imine). Delayed release of the perfume (ketone or aldehyde) from the reaction product is obtained, which is believed to occur by mechanisms including hydrolysis, photochemical cleavage, oxidative cleavage or enzymatic cleavage. The amine reaction product is preferably preformed before incorporation into the laundry and cleaning composition, to enable better control of the yield and purity of the reaction product and avoid possible interaction with perfume present in the composition. Where the laundry and cleaning compositions include perfume, the amine reaction product is preferably incorporated in the composition separately from the perfume, for better control of the amine reaction product and subsequent perfume release therefrom.

WO 00/02982 is generally similar to WO 00/02981, but requires the use of an amino functional polymer comprising at least one primary amine and/or secondary amine group.

It is also known to use various 4-aminobenzoate esters (i.e. para-aminobenzoate esters) in perfumed products because of the sunscreen properties of the esters. For example, U.S. Pat. No. 3,330,730 discloses aerosol sunscreen compositions including N,N-dimethyl isoamyl para-aminobenzoate or glyceryl para-aminobenzoate. DE 1492322 concerns the use of UV-absorbing substances as additives for cosmetics and discloses, e.g., use of monoglyceryl p-aminobenzoate in a toilet water.

EP 1004652 concerns use of various aminobenzoate derivatives, particularly methyl ortho-aminobenzoate (methyl anthranilate), as adjuvants for reducing adaptation to odour-emitting substances such as perfumes.

The present invention is based on an alternative approach to enhancing perfume efficacy, not using pro-perfumes or pro-fragrances, which aims to overcome the problems discussed above.

SUMMARY OF THE INVENTION

In one aspect the present invention provides use of a substantially odourless aromatic amine trapping agent in a composition including perfume, for the purpose of enabling the perfume and trapping agent to react chemically spontaneously and reversibly to form a reaction product from which the perfume can be released.

The present invention thus uses a different approach to the prior art using pro-perfumes. In contrast to a pro-perfume, the reaction product formed in the present invention is not used by being included as such in a mixture of perfumes or perfumed product, but instead the perfume and trapping agent are included in a mixture of perfumes or perfumed product where they react spontaneously in situ to form a transient reaction product for subsequent release of the perfume.

The expression "substantially odourless aromatic amine trapping agent" is used to mean an aromatic amine (i.e. an amine including an aromatic ring) that has little or no odour properties, ie little or no discernible odour or smell under normal ambient conditions of pressure (atmospheric) and temperature (about 20° C.). The trapping agent thus does not significantly add to the odour of the composition.

Odour intensity can be measured and qualified by various known techniques, including the Odour Intensity Index method as disclosed in EP-A-0404470, which is based on a comparison by trained assessors with benzyl acetate diluted in dipropylene glycol.

In practising the invention, the perfume and trapping agent react together spontaneously, ie without requiring any external driving force such as the application of heat, light etc at normal ambient conditions of pressure (atmospheric) and temperature (about 20° C.). In the resulting reaction product the perfume may be protected against degradation, premature evaporation etc, with the perfume being releasable from the reaction product, in a manner possibly analogous to that of a pro-perfume.

Further, a single trapping agent can react with a number of different perfumes (either in the same or different perfume compositions) to give a range of different corresponding reaction products, rather than it being necessary separately to synthesise a separate respective pro-perfume for each different perfume to be protected. A single trapping agent can thus be very versatile.

The perfume can be released from the reaction product by a number of different possible mechanisms, including hydrolysis (possibly simply on exposure to moisture in air and/or exposure to water), thermolysis, photochemical cleavage, oxidative cleavage and enzymatic cleavage. For example the reaction product may hydrolyse to release the perfume on exposure to water under appropriate conditions of pH etc.

The reaction product is preferably stable in a perfume composition or perfumed product under normal conditions of formulation and storage, with the perfume being released during or following normal usage as desired. For example, many products are formulated to have alkaline pH during storage and use, and in such cases it is desirable for the reaction product to be stable under alkaline conditions. In use of the product the reaction product is desirably deposited and retained on a surface, eg fabric, skin. When pH is reduced to become more acid, eg on exposure to rinse water, enzymes in skin flora etc, the reaction product hydrolyses mores rapidly to release the perfume. Such mechanisms are described, eg in WO 99/46318 on page 11.

It is possible that some perfume may be released from the reaction product during storage, as a result of the reversible nature of the reaction. A benefit is nevertheless obtained as a result of the perfume being at least partially protected from degradation etc during storage.

The trapping agent is preferably non-polymeric in nature, ie comprising no more than 5 monomer units.

The trapping agent may generally be any of the amine-containing materials disclosed in WO 00/02981 and WO 00/02982, although the trapping agent is preferably a primary amine.

Desirably the trapping agent is an amino derivative of benzoic acid or a benzoic acid ester, possibly a lower alkyl (ie having from 1 to 5 carbon atoms) ester.

Most preferably the trapping agent is an amino derivative of an ortho- or para-benzoic acid ester. Ortho- and para-derivatives tend to have greater stability than corresponding meta-derivatives, hence the preference. Para-derivatives are preferred to ortho-derivatives, generally being less coloured and less odiferous. Para-aminobenzoate esters have the following structure:

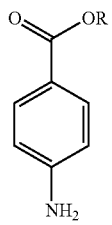

Para-aminobenzoate esters are well known sunscreen agents, as noted above, so use of such materials as trapping agents is likely to have the added benefit of the trapping agent acting as an ultraviolet protection agent for skin and/or hair and for protecting perfumes against ultraviolet induced degradation.

The trapping agent may, for example, comprise methyl para-aminobenzoate (or methyl 4-aminobenzoate) (with R being $CH_3$ in the structure above) (which has a calculated log P value, as discussed below, of 1.96) or methyl meta-aminobenzoate, both of which have a slight but not significant odour and so constitute substantially odourless materials. The para-compound is preferred to the meta-compound for reasons of stability. Methyl ortho-aminobenzoate (methyl anthranilate) is highly odiferous and indeed is a known perfume, and so is unsuited for use as a trapping agent in the invention as it would substantially affect the odour properties of the composition. Initial experiments with such smaller aminobenzoate esters have worked well.

However, there is possibly a preference for use of larger aminobenzoate esters, having lower volatility and higher calculated log P values, as discussed below. It is also preferred in some cases to use aminobenzoate esters having branched alkyl groups, as these can display better solubility profiles.

Where the trapping agent is an ester, hydrolysis of the reaction product may result in release of the alcohol from which the ester is formed, depending on reaction conditions such as pH etc and depending upon the exact ester. Alcohol release may have associated benefits, such as contribution to odour or antimicrobial effects.

The trapping agent preferably has a calculated log P value in the range 4 to 10, more preferably 5 to 9, where P stands for the octanol/water partitioning coefficient of a material, ie the ratio between its equilibrium concentration in octanol and water, which is a measure of hydrophobicity. High partitioning coefficient values are more conveniently given in the form of their logarithm to the base 10, log P. While log P values can be measured experimentally, and measured log P data is available for many perfumes, log P values are most conveniently calculated. There are several recognised calculation or estimation methods available commercially and/or described in the literature (see for example A Leo, Chem.Rev 93(4), 1281–1306, (1993), "Calculating log P oct from structures"). Generally these models correlate highly but may for specific materials produce log P values which differ in absolute terms (by up to 0.5 log units or even more). However, no one model is universally accepted as the most accurate across all compounds. This is particularly true for estimates on materials of high log P (say 4 or greater). In the present specification, calculated log P values are obtained using the estimation software of Toronto-based Advanced Chemistry Development Inc (ACD) which is well-known to the scientific community, and accepted as providing high-quality predictions of log P values. References to calculated log P values thus mean values obtained using the ACD software. Examples of preferred trapping agents with higher log P values are given below.

Log P values indicate the substantivity (ie ability to bind) of a material to hydrophobic surfaces eg cloth and hair. Materials with a calculated log P in the preferred ranges should well be able to survive typical machine washing and hair washing processes without being dissolved and washed away.

The reaction product preferably has a higher calculated log P value than that of the trapping agent from which it is formed, for enhanced substantivity of the reaction product.

The perfume preferably includes a carbonyl group (—C=O) and is preferably an aldehyde, ketone or carboxylic acid, with aldehydes currently being favoured. The perfume may include additional functional groups such as alcohols, esters, ethers etc. The perfume may be saturated or unsaturated, linear, branched or cyclic. The perfume preferably includes at least 7 carbon atoms. Many perfumes satisfying these requirements are well known to those skilled in the art, and examples are given on pages 13 to 15 of WO 99/46318.

A perfume containing a carbonyl group may react with an amine trapping agent in a condensation reaction to form a Schiff's base, in known manner.

In one preferred embodiment the perfume comprises an aldehyde which spontaneously and reversibly undergoes a condensation reaction with an amine trapping agent to form a Schiff's base and water in the following general reaction scheme:

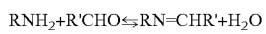

The reaction is reversed by hydrolysis, eg on exposure to water at appropriate pH in use as discussed above, releasing the perfume.

The reaction product is preferably also substantially odourless as defined above, or is at least less strongly odiferous than perfume materials in the composition, so that the odour properties of the composition are not affected, or are not adversely affected, by the presence of the reaction product.

In the simplest case, the composition consists of a perfume and trapping agent. More usually, however, the composition will include one or more additional perfumes, possibly a large number of different perfumes, to produce a mixture having desired odour properties, typically mixed with or dissolved in suitable solvent or mixed with solid substrate. The presence of the trapping agent may affect the odour properties of a perfume composition, particularly a composition including a number of different perfume ingredients, possibly reducing the impact of the perfume, so the composition may require some rebalancing or reformulation to compensate.

Other perfumes that can be included in the composition include natural products such as extracts, essential oils, absolutes, resinoids, resins, concretes etc, and also synthetic materials such as hydrocarbons, alcohols, aldehydes, ketones, ethers, acids, esters, acetals, ketals, nitrites etc, including saturated and unsaturated compounds, aliphatic, carbocyclic and heterocyclic compounds, as is well known to those skilled in the art. Such perfumes are mentioned, for example, in S. Arctander, Perfume and Flavor Chemicals (Montclair, N.J., 1969), in S. Arctander, Perfume and Flavor Materials of Natural Origin (Elizabeth, N.J., 1960) and in "Flavor and Fragrance Materials—1991", Allured Publishing Co. Wheaton, Ill. USA.

Solvents which can be included in the composition include those known for perfumery use, such as ethanol, isopropanol, diethyleneglycol monoethyl ether, dipropylene glycol, diethyl phthalate, triethyl citrate, isopropyl myristate, etc, or mixtures thereof, as is well known to those skilled in the art.

The composition can be used in or constitute a wide range of perfumed products including fabric care products such as fabric washing powders, liquids and fabric softeners, fabric ironing sprays; dishwasher products; detergents and household cleaning, scouring and disinfection products; air fresheners, room sprays and pomanders; soaps, bath and shower gels, shampoos, hair conditioners and other personal cleansing products; fine fragrances; cosmetics such as creams ointments, toilet waters, preshave, aftershave, skin and other lotions, talcum powders, body deodorants and antiperspirants, etc.

The trapping agent is typically added to a perfume (or mixture of a number of different perfumes) possibly combined with one or more solvents and/or solid substrates to produce a perfume composition that may otherwise be of conventional formulation. The resulting perfume composition may then be used in conventional manner, eg being included in a perfumed product. It is also possible for the trapping agent to be added to a conventional perfumed product, to react with perfume in the product.

The trapping agent is suitably present in a composition in an appropriate amount to react with the perfume, and typically is present in an amount in the range 0.1% to 15%, preferably 0.1% to 5%, by weight of the weight of the composition.

The trapping agent is typically present in a composition in an amount in the range 0.001% to 10% by weight of the weight of the product.

The perfume and/or trapping agent may be encapsulated, separately or together, in known manner, particularly prior to addition to a product presenting a hostile environment.

The invention also provides a method of making a perfume composition, comprising mixing together a perfume and a substantially odourless aromatic amine trapping agent that chemically react together spontaneously and reversibly to form a reaction product from which the perfume can be released.

In a further aspect the invention provides a method of modifying a perfume composition or perfumed product, comprising adding to the perfume composition or perfumed product a substantially odourless aromatic amine trapping agent that chemically reacts spontaneously and reversibly with a perfume in the composition or product to form a reaction product from which the perfume can be released.

The invention also provides a method of preserving a perfume, prolonging perfume life or delaying perfume release in a perfume composition or perfumed product, comprising adding to the perfume composition or perfumed product a substantially odourless aromatic amine trapping agent that chemically reacts spontaneously and reversibly with the perfume to form a reaction product from which the perfume can be released.

Also included within the scope of the invention is a method of modifying a perfumed product, comprising adding to the product a perfume and a substantially odourless aromatic amine trapping agent that chemically react together spontaneously and reversibly to form a reaction product from which the perfume can be released.

The invention also provides a perfume composition, comprising a perfume and a substantially odourless aromatic amine trapping agent that chemically react together spontaneously and reversibly to form a reaction product from which the perfume can be released, wherein the trapping agent is non-polymeric and has a calculated log P in the range 4 to 10, but excluding the trapping agent having the formula

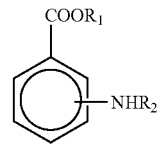

where $R_1$ is a C1 to C8 lower alkyl group or a C7 to C9 aralkyl group and $R_2$ is a hydrogen atom or a C1 to C8 lower alkyl group.

The composition of the invention uses a trapping agent an amine having a higher calculated log P value than materials disclosed (for different purposes) in perfume compositions, e.g. glyceryl para-aminobenzoate disclosed in U.S. Pat. No. 3,330,730 and DE 1492322 which has a calculated log P of 0.26. Further ethyl 4-aminobenzoate as used e.g. in WO 00/02981 to make a pro-perfume has a calculated log P of 2.49. The amine used as the trapping agent in the composition of the invention is further distinguished from the disclosures of EP 1004654 by the specific exclusion of the materials covered thereby.

The trapping agent is preferably as described above in connection with the first aspect of the invention, and desirably comprises a para-aminobenzoate ester.

Particularly preferred trapping agents include the following six specific materials (which are all substantially odourless):

1) 3,7 dimethyloctyl 4-aminobenzoate (referred to herein as QTR 54 for brevity) i.e. the tetrahydrogeranyl ester. This has a calculated log P of 6.37 and the following structure:

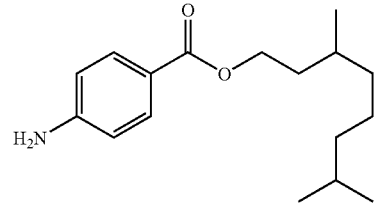

2) 3,5,5 trimethylhexyl 4-aminobenzoate (referred to herein as QTR57 for brevity) i.e. the inonyl ester. This has a calculated log P of 5.66 and the following structure:

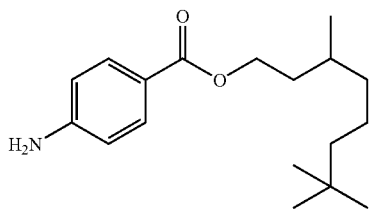

3) 2(E/Z)3,7,dimethyloct-2,6-dienyl 4-aminobenzoate. This has a calculated log P of 5.90 and the following structure:

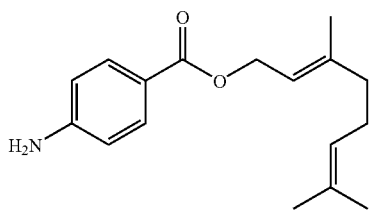

The above three materials are known per se, but perfumery use of these materials is novel.

4) 3-methyl-5-phenylpentyl 4-aminobenzoate. This has a calculated log P of 5.82 and the following structure:

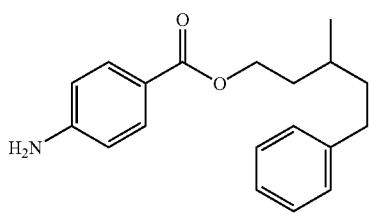

5) 3,7,dimethyloct-6-enyl 4-aminobenzoate. This has a calculated log P of 6.06 and the following structure:

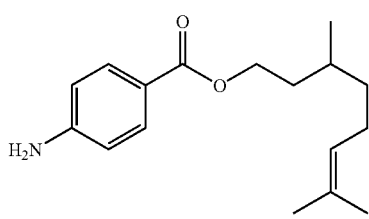

6) 3[(4-aminobenzoyl)oxy]-2ethylhexyl 4-aminobenzoate. This has a calculated log P of 6.52 and the following structure:

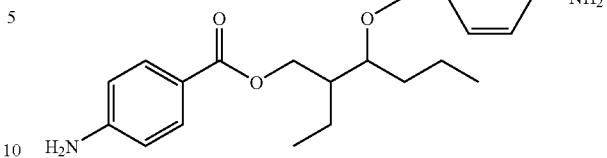

The above three materials are novel per se. Synthesis details are given below. The invention encompasses these materials as novel compositions of matter and their use in perfumery.

The currently favoured trapping agent is QTR54 (3,7 dimethyloctyl 4-aminobenzoate).

The corresponding 2-aminobenzoate versions of the above six materials may also be used, although these are generally less favoured, tending to be more coloured. The 2-aminobenzoate version of QTR54 has a log P of 6.45, while that of QTR57 has a log P of 5.74.

In perfume compositions in accordance with the invention, the perfume is preferably as described above in connection with the first aspect of the invention.

The trapping agent effectively functions as a perfume fixative, prolonging the effect of the perfume and so prolonging perfume life, generally by delaying the loss of volatile top note fragrance materials.

The trapping agent, particularly higher molecular weight materials (having a molecular weight of at least 250 and a calculated log P of at least 5), in addition to functioning by the spontaneous reversible reaction discussed above, may also function to give useful perfume fixative effects by other mechanisms with a wide range of perfumes.

Thus, the invention also covers use of a substantially odourless amine, particularly higher molecular weight materials, and especially the six specific preferred materials detailed above, as a perfume fixative or as a perfume ingredient.

The invention also includes within its scope a perfume fixative comprising a substantially odourless amine, particularly higher molecular weight materials, and especially the six specific preferred materials detailed above.

In another aspect, the invention provides a perfume fixative comprising a substantially odourless aromatic amine that is non-polymeric and has a calculated log P in the range 4 to 10, but excluding an amine having the formula:

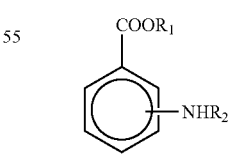

where $R_1$ is a C1 to C8 lower alkyl group or a C7 to C9 aralkyl group and $R_2$ is a hydrogen atom or a C1 to C9 lower alkyl group. The amine fixative is preferably a higher molecular weight material, as discussed above, and is more preferably one or more of the six specific preferred materials discussed above.

The invention will be further described, by way of illustration, in the following Examples. The Examples refer to the accompanying drawings, in which.

Examples 1 to 3 concern preliminary odour assessment experiments using methyl 4-aminobenzoate as an example of a trapping agent in accordance with the invention. All odour assessments were carried out by a panel of 5 trained assessors who assessed the samples on the basis of odour strength and rated the samples on a scale of 0–5. The results were pooled and expressed in the form of a bar graph.

EXAMPLE 1

Hair Conditioner

Experiments were carried out with a hair conditioner having the following base formulation:

|  | % w/w |
|---|---|
| LAUREX CS | 0.9 |
| AMMONYX 4A | 2.8 |
| NATROSOL 250HHR | 0.7 |
| CITRIC ACID | 0.3 |
| MERQUAT PLUS 3331 | 2 |
| PRESERVATIVE | 0.1 |
| COLOUR | As required |
| PURIFIED WATER | to 100 |

Laurex CS, Ammonyx 4A, Natrosol 250HHR and Merquat Plus 3331 are Trade Marks.

Perfume was added to the base formulation at a level of 0.8% w/w. The perfume has the following base formulation in parts by weight:

| alcohol (straight chain) C-10 | 7 |
|---|---|
| citronellol | 16 |
| diphenyl oxide | 2 |
| geraniol | 48 |
| linalol | 2 |
| aldehyde C-10 (straight chain - decanal) | 10 |
| aldehyde MNA (methyl nonyl aldehyde) | 5 |
| Ligustral (Ligustral is a Trade Mark) | 10 |

A control formulation was produced by adding the perfume base formulation to the conditioner base formulation (control). A composition using a trapping agent in accordance with the invention was produced by adding to the conditioner base formulation the perfume base formulation additionally including 25 parts by weight of methyl 4-aminobenzoate (accord+additive).

Experiments were carried out on respective samples of cut human hair about 20 cm in length bound at one end to form a bundle. Respective hair samples were wetted with water and thoroughly massaged with 10 g samples of either the control formulation or the accord+additive formulation. The hair samples were rinsed with water thoroughly and hung to dry. Odour assessments were made by the panel of assessors while the samples were still wet. The samples were then blow-dried with a hair dryer for 3 minutes and the samples reassessed. The odour assessment results were as follows:

|  | wet | dry |
|---|---|---|
| Control | 19 | 8 |
| Accord + additive | 20 | 15 |

Figure 1:
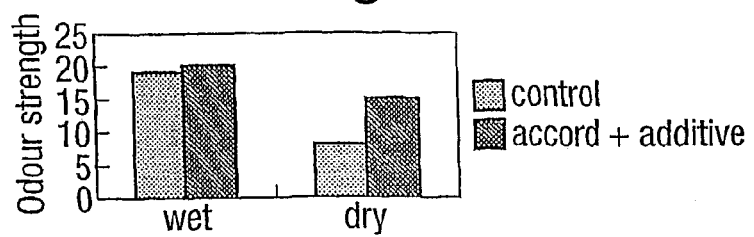
FIG. 1 is a bar graph of odour strength of results for Example 1 for hair conditioner formulations.

The results are shown in FIG. 1. These show that on the wet samples there was little difference in odour strength, while on the dry samples the one treated with a composition including a trapping agent in accordance with the invention had a substantially stronger odour.

EXAMPLE 2

Hard Surface Cleaner

Experiments were carried out with a hard surface cleaner having the following formulation (in % by wt):

| Imbentin | 5% |
|---|---|
| Butyl diol | 3% |
| Sodium cumene sulphonate | 1% |
| Perfume | 0.5% |
| Water | to 100%. |

The perfume was as specified in Example 1, both with methyl 4-aminobenzoate (accord+additive) and without methyl 4-aminobenzoate (control).

The formulations were left to stand for 20 minutes then diluted 1:20 with water. 1 ml of each formulation was placed on a respective 20 cm×20 cm glazed tile and spread evenly with a paintbrush. Odour assessments were made as described above 15 min and 45 min after application to the tiles. The results were as follows:

|  | 15 min | 45 min |
|---|---|---|
| Control | 12 | 5 |
| Accord + additive | 10 | 9 |

Figure 2:
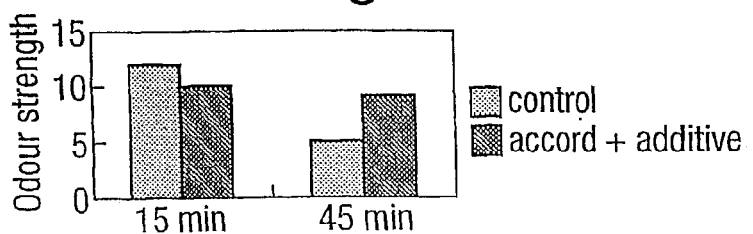
FIG. 2 is a bar graph of odour strength of results for Example 2 for hard surface cleaner formulations.

The results are shown in FIG. 2. These show that while the control had slightly greater odour after 15 min, the composition with a trapping agent in accordance with the invention had a substantially stronger odour after 45 min.

EXAMPLE 3

Cologne on Smelling Strips

Experiments were carried out using a fruity, floral cologne accord having the following composition (in parts by weight) at a level of 10% by weight in ethanol:

| | |
|---|---|
| allyl ionone | 0.2 |
| Applinal (Trade Mark) | 0.3 |
| cis-3-hexenyl acetate | 0.2 |
| cis-jasmone | 1.2 |
| damascone alpha | 0.1 |
| dihydromyrcenol | 3.0 |
| ethyl acetate | 0.2 |
| ethyl linalol | 15.0 |
| hexyl acetate | 1.0 |
| ionone beta | 1.0 |
| linalol | 8.0 |
| linalyl acetate | 4.0 |
| Ligustral (Trade Mark) | 0.2 |
| methyl dihydrojasmonate | 48.4 |
| nonalactone gamma | 0.2 |
| patchouli DM pure | 0.2 |
| prenyl acetate | 1.5 |
| peche pure | 3.0 |
| vanillin (10% in dipropylene glycol) | 1.5 |

Control cologne was as specified above while cologne with a trapping agent in accordance with the invention (accord+additive) also included 0.2 parts by weight of methyl 4-aminobenzoate. Both colognes were applied to standard perfumery blotters or smelling strips and were left in the open under ambient conditions. Odour assessments were carried out 1 hr, 4 hr and 16 hr after application. The results were as follows:

| | 1 hr | 4 hr | 16 hr |
|---|---|---|---|
| Control | 15 | 8 | 3 |
| Accord + additive | 25 | 18 | 10 |

Figure 3:
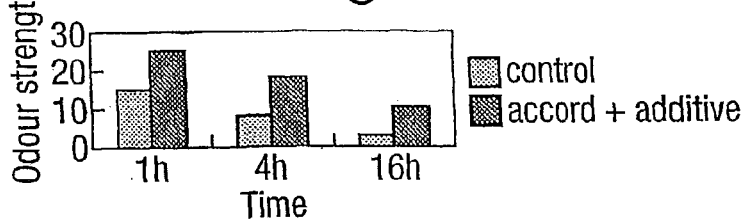
FIG. 3 is a bar graph of odour strength of results for Example 3 for cologne on smelling strips.

The results are shown in FIG. 3. The results show that in all cases the cologne with the trapping agent in accordance with the invention has substantially longer lasting, green character odour than the control, with the difference in odour strength tending to increase with time, reflecting the enhanced perfume life obtained by use of a trapping agent in accordance with the invention.

Further experiments were carried out with 3,7 dimethyloctyl 4-aminobenzoate (QTR54) and 3,5,5 trimethylhexyl 4-aminobenzoate (QTR57) in a biodegradable quaternary ammonium fabric conditioner comprising a 5% solution in water of compound C as described in Example 1 of U.S. Pat. No. 4,137,180.

Gas chromatography (GC) analysis was performed using the following parameters:
HP 6890 GC
Cool on-column injection
50° C. to 250° C. at 5° C./min
SE 54 column
Nitrogen carrier gas Synthesis details for QTR54 and QTR57 and also various other trapping agents in accordance with the invention (the last 3 of which are novel materials per se) are as follows:

NMR spectra were measured using a Jeol Eclipse +400 spectrometer at 400 MHz $^1$H in deuteriochloroform solution using the residual chloroform at δ7.25 as internal standard or at 100 MHz $^{13}$C in deuteriochloroform solution with CDCl$_3$ (middle peak) at 77 ppm as internal standard. Mass spectra were measured using a Finigan MAT GCQ GC/Mass Spec.

(3,7 dimethyl octyl) 4-aminobenzoate (QTR54)

Na metal (200 mg, cat.) was added to a suspension of methyl 4-aminobenzoate (45 g, 300 mmol), tetrahydrogeraniol (48 g, 300 mmol) in PhMe (250 mL). The suspension was heated under reflux for 3 hours with the azeotropic removal of MeOH. The mixture was cooled and filtered through a plug of silica (400 mL) with cyclohexane: EtOAc (9:1) as eluant to give the ester (24 g, 30%) as a pale yellow oil.

δc (100 MHz, CDCl$_3$) 19.72, 22.69, 22.79, 24.72, 28.03, 30.06, 35.75, 37.25, 39.28, 63.04, 113.83, 120.10, 131.62, 150.88, 166.87 ppm. Mass spectrum M(+) 277.

(3,5,5 trimethyl hexyl) 4-aminobenzoate (QTR57)

Sodium metal (1 g cat.) was added to ethanol (30 mL) to give a solution which was added to a suspension of ethyl 4-aminobenzoate (175 g, 1.06 mol) and 3,5,5 trimethyl hexanol (200 g, 1.4 mol) in cyclohexane (300 mL). The suspension was heated under reflux for 24 hours with the azeotropic removal of ethanol.

The cyclohexane was removed by distillation to give a tan coloured paste. Short path distillation gave the ester as a colourless oil (b.p. 168–170° C. at 0.01 mm Hg) (68 g, 25%) which crystallized. Recrystallization of a small sample from methanol gave the ester as waxy plates m.p 72–74° C.

δc (100 MHz, CDCl$_3$) 22.64, 26.28, 29.92, 31.07, 37.98, 50.98, 62.90, 113.74, 120.06, 131.48, 150.68, 166.73 ppm. Mass spectrum M(+) 263

2(E/Z) (3,7 dimethyl oct-2,6-dienyl) 4-aminobenzoate

Sodium hydride (600 mg, cat. 60% disp in oil) was added to a suspension of methyl 4-aminobenzoate (50 g, 330 mmol), geraniol (51 g, 330 mmol) in PhMe (100 mL). The suspension was heated under reflux for 8 hours with the azeotropic removal of MeOH. The mixture was cooled and filtered through a plug of silica (400 mL) with cyclohexane: isopropanol (95:5) as eluant to give the crude ester (X) as a pale yellow oil. Recrystallization from methanol gave the ester (11 g, 12%) as needles.

δc (100 MHz, CDCl$_3$) 16.62, 17.78, 25.75, 26.41, 39.63, 61.40, 113.82, 118.92, 120.11, 123.90, 131.69, 131.85, 141.81, 150.85, 166.82 ppm. Mass spectrum M(+) 273

3[(4-aminobenzoyl)oxy]-2ethylhexyl 4-aminobenzoate

NaH (60% dispersion in oil, 1 g, cat) was added in one portion to a suspension of methyl 4-aminobenzoate (50 g, 330 mmol), octylene glycol (24 g, 165 mmol) in toluene (150 mL). The mixture was heated under reflux for 9 hours then cooled. The suspension was filtered through a plug of silica (200 mL) with cyclohexane then cyclohexane:ethyl acetate (7:3) as eluants gave a mixture of the mono and bis esters as a complex mixture of diastereoisomers.

δc (100 MHz, CDCl$_3$) 11.91, 14.08, 19.07, 19.18, 21.44, 33.41, 34.24, 37.00, 43.09, 43.13, 63.64, 63.85, 64.67, 74.04, 113.84, 113.86, 119.70, 119.91, 131.67, 131.70, 151.07, 151.09, 166.42, 166.45, 166.90 ppm. Mass Spectrum monoester M(+) 265 and bis ester Mass Spectrum M(+) 384

(3,7 dimethyl oct-6-enyl) 4-aminobenzoate

Sodium methoxide (2.5 g, cat.) was added to a suspension of ethyl 4-aminobenzoate (10 g, 60 mmol), citronellol (15 g, 90 mmol) in cyclohexane (100 mL). The suspension was heated under reflux for 8 hours with the azeotropic removal of EtOH. The mixture was cooled and filtered through a plug of silica (400 mL) with cyclohexane:isopropanol (95:5) as eluant to give the ester (5.0 g, 30%)as a pale yellow solid.

δc (100 MHz, CDCl$_3$) 19.61, 59.67, 33.37, 35.63, 38.89, 62.81, 113.86, 120.08, 125.72, 128.45, 131.65, 142.76, 150.88, 166.84 ppm. Mass spectrum M(+) 275

(3-methyl-5-phenyl-pentyl)-4-aminobenzoate

Sodium hydride (600 mg, cat. 60% disp in oil) was added to a suspension of methyl 4-aminobenzoate (30 g, 19 mmol), 3-methyl, 5-phenyl pentanol (36 g, 20 mmol) in PhMe (100 mL). The suspension was heated under reflux for 24 hours with the azeotropic removal of MeOH. The mixture was cooled and filtered through a plug of silica (400 mL) with cyclohexane:isopropanol (95:5) as eluant to give the ester as a pale yellow oil (15 g, 25%) which slowly crystallized.

δc (100 MHz, CDCl$_3$) 17.64, 19.50, 25.39, 25.70, 29.55, 35.58, 37.00, 62.85, 113.76, 120.16, 124.62, 131.30, 131.53, 150.64, 166.70 ppm. Mass spectrum M(+) 297

EXAMPLE 4

Samples

Control perfume: delta damascone (0.1 g) in Fabric Conditioner (50 g)

Test perfume: delta damascone (0.1 g)+QTR 54 (0.2 g) in Fabric Conditioner (50 g)

The headspace above the two fabric conditioners was tested by GC, giving the following results:

| GC areas | headspace above liquid conditioner |
|---|---|
| damascone | 15529026 |
| damascone + Fixative A | 4376011 |

Figure 4:
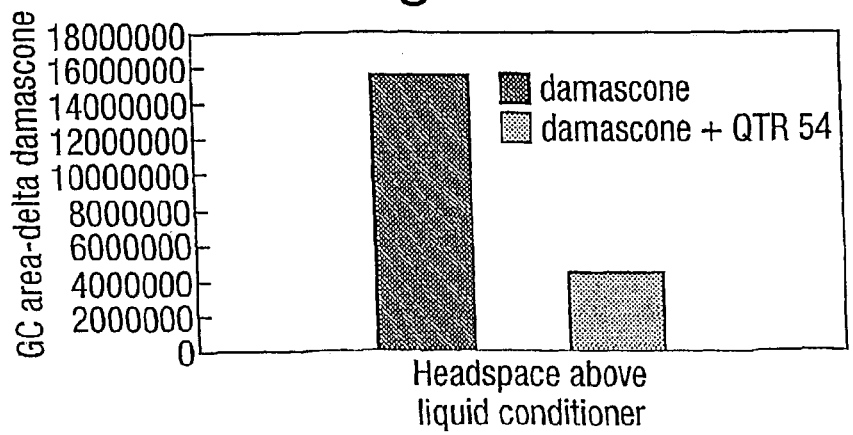
FIGS. 4 and 5 are bar graphs of GC results for Example 4.

The results are shown in FIG. 4.

Washing Protocol

Fabric conditioner (2 g) containing either control or test perfumes (0.2%), was suspended in pure deionized water (150 mL). 7 g (10×10 cm) of terry towelling cotton cloth was soaked and shaken in the solution for 30 min at 40° C. After washing, the cloth sample was squeezed down to a mass of 20 g, and then shaken for 1 min suspended in pure deionized water (150 mL). The cloth was squeezed down to 20 g and allowed to line-dry for 4 hours, before being submitted for GC analysis of headspace above the cloth. The results were as follows:

| GC areas | headspace above dry cloth |
|---|---|
| damascone | 7080 |
| damascone + Fixative A | 32828 |

Figure 5:
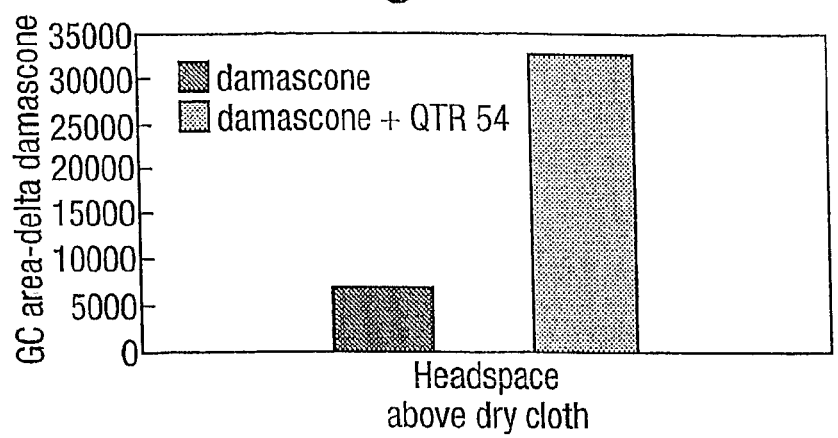

The results are shown in FIG. 5.

Thus from these experiments it can be seen that the aminobenzoate fixative or trapping agent QTR54 has the effect of reducing the headspace of delta damascone in fabric conditioner (in product) by a factor of 3.5 relative to a delta damascone control. After the cloth is line dried for 4 hours this trend is reversed, with the level of delta damascone by headspace above the cloth being 4.6 fold less than the cloth washed with fabric conditioner containing both delta damascone and the aminobenzoate fixative. This is due to the enhanced substantivity of delta damascone to the cloth in the presence of QTR54.

EXAMPLE 5

Similar experiments to those described in Example 4 were carried out using the trapping agent or fixative QTR57 with the perfume decanal. GC analysis was performed as before, and substantivity on the cloth calculated.

Substantivity on Cotton Towelling

The substantivity is expressed as a ratio of the amount of perfume ingredient deposited onto the cloth over that initially present in the wash water. Thus 100% substantivity represents total deposition of the ingredient onto the cloth from the wash solution.

Samples

Control perfume: decanal (0.1 g) in Fabric Conditioner (50 g)

Test perfume: decanal (0.1 g)+QTR 57 (0.2 g) in Fabric Conditioner (50 g)

Figure 6:
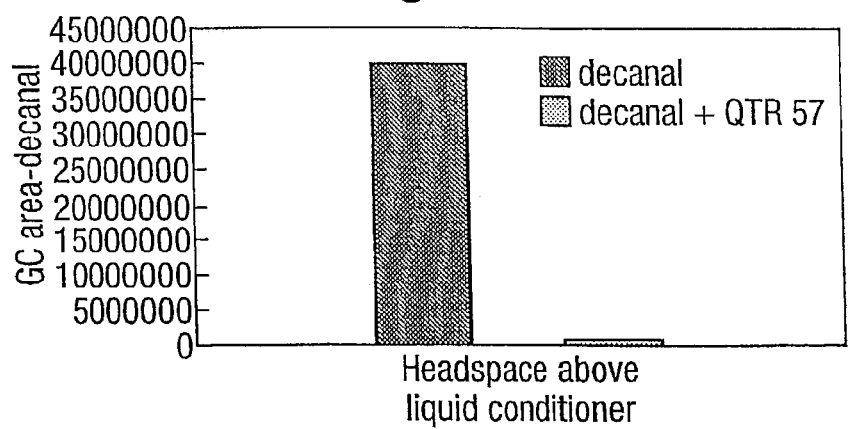
FIGS. 6 and 7 are bar graphs of GC results for Example 5.

The headspace above the two fabric conditioners was tested by GC, and the results shown in FIG. 6.

Washing Protocol

Figure 7:
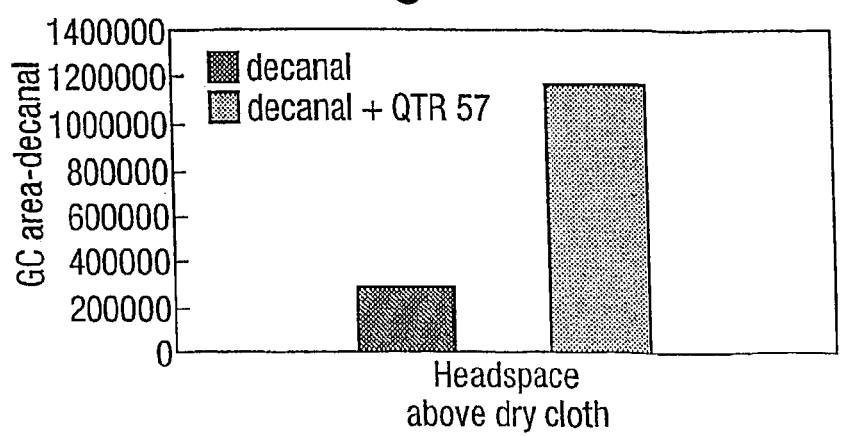

Fabric conditioner (1 g) containing either control or test perfumes (0.2%), was suspended in pure deionized water (150 mL). 7 g (10×10 cm) of terry towelling cotton cloth was soaked and shaken in the solution for 30 min at 40° C. After washing, the cloth sample was squeezed down to a mass of 20 g, and then shaken for 1 min suspended in pure deionized water (150 mL). The cloth was squeezed down to 20 g and allowed to line-dry for 4 hours, before being submitted for extraction and headspace analysis. Thus, the headspace above the cloth was analysed by GC, as in Example 4, and the results are shown in FIG. 7. In addition, the cloth was subjected to solvent extraction, as described in the following extraction protocol.

Extraction Protocol

Half of each terry towelling cloth sample was submitted to extraction. The cloth (3.5 g) was extracted with ethyl acetate (50 mL). An internal standard (80 μl of a 0.04% fluoronaphthalene solution) was added to the mixture. The solvent extract was concentrated by distillation and analyzed by on-column GC.

Quantification and Results

Quantification of the decanal extracted from the cloth was carried out using an internal standard (fluoronaphthalene). The results are given below:

| | Amount of decanal extracted/mg per 3.5 g of cloth | Amount of decanal extracted/mg per 7 g of cloth | Initial amount of decanal in 150 ml water/mg | Decanal substantivity on cotton cloth/% |
|---|---|---|---|---|
| Control | 0.028 | 0.056 | 2 | 1.4 |
| test | 0.068 | 0.136 | 2 | 6.8 |

These results thus show that the presence of the aminobenzoate fixative improves deposition of decanal (approx. 5 fold increase) onto terry towelling cloth from fabric conditioner in aqueous solution under simulated wash conditions.

EXAMPLE 6

Similar experiments to those described in Example 5 were carried out using QTR54 and a perfume comprising a mixture of aldehyde MNA (methyl nonyl acetaldehyde=2- methyl undecanal) and Lilial (Lilial is a Trade Mark) which is a perfumery ingredient comprising [4-(2,2-dimethylethyl) phenyl]-2-methyl propanal.

Samples

Control perfume: aldehyde MNA (0.02 g)+Lilial (0.08 g) in Fabric Conditioner (50 g)

Test perfume: aldehyde MNA (0.015 g)+lilial (0.06 g)+QTR 54 (0.15 g) in Fabric Conditioner (50 g)

Washing Protocol

Fabric conditioner (2 g) containing either control or test perfumes, was suspended in pure deionised water (150 mL). 6 g Terry towelling cotton cloth (6 g, approx.10×10 cm) was soaked and shaken in the fabric conditioner solution for 30 min at 40° C. After washing, the cloth sample was squeezed down to a mass of 20 g, and then shaken for 1 min with pure deionized water (150 mL). The cloth was squeezed down to 20 g and allowed to dry on a line for 5 hours, before being submitted to solvent extraction and GC analysis as described below.

Extraction Protocol

Half of each cloth sample was submitted to extraction. The terry towelling cloth (3.0 g) was extracted with ethyl acetate (50 mL). An internal standard (80 μl of a 0.04% fluoronaphthalene solution) was added to the mixture. The solvent extract was concentrated by distillation and analyzed by on-column GC.

Quantification and Results

Quantification of the Lilial and aldehyde MNA extracted from the cloth were carried out using an internal standard (fluoronaphthalene) and using Lilial and aldehyde MNA calibration standards.

Figure 8:
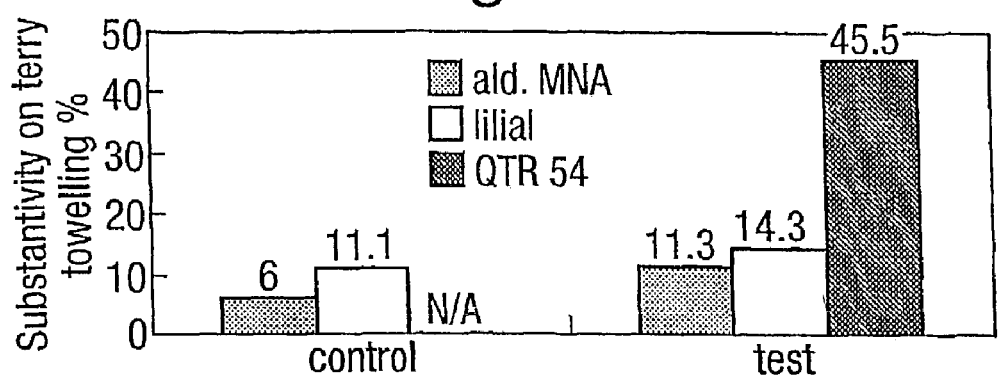
FIG. 8 is a bar graph of substantivity results for Example 6.

The results are given below, with the substantivity results being shown in FIG. 8.

|  | Amount of Lilial extracted/mg per 3.0 g of cloth | Amount of Lilial extracted/mg per 6 g of cloth | Initial amount of Lilial in 150 ml water/mg | Lilial substantivity on cotton cloth/% |
|---|---|---|---|---|
| Control | 0.178 | 0.356 | 3.2 | 11.1 |
| test | 0.172 | 0.344 | 2.4 | 14.3 |
|  | Amount of aldehyde MNA extracted/mg per 3.0 g of cloth | Amount of Aldehyde MNA extracted/mg per 6 g of cloth | Initial amount of aldehyde MNA in 150 ml water/mg | Aldehyde MNA substantivity on cotton cloth/% |
| Control | 0.024 | 0.048 | 0.8 | 6.0 |
| test | 0.034 | 0.068 | 0.6 | 11.3 |

Thus from this experiment it can be seen that there is little effect of the aminobenzoate fixative QTR54 on the deposition of Lilial onto cloth. Lilial is already a reasonably fabric substantive aldehyde (11% deposition). The effect of the aminobenzoate fixative on the deposition of aldehyde is more evident from the data. The fixative results in a 2 fold increase in the amount of aldehyde MNA deposited on cloth from fabric conditioner.

Further experiments were carried out to demonstrate spontaneous reversible formation of a complex.

EXAMPLE 7

Various mixtures of 3,7 dimethyloctyl 4-aminobenzoate (QTR54) and 2 methyl butyraldehyde were allowed to stand and then analysed by gas chromatography. (Hewlett Packard HP-1 column 25M×0.2 mm ID Hydrogen carrier gas, 1.5 mL/min). All components were confirmed by GC/MS 3,7 dimethyloctyl 4-aminobenzoate 2-methyl butyraldehyde complex M(+)345 isomers 3,7 dimethyloctyl 4-aminobenzoate cyclohexyl carbaldehyde complex M(+)371.

A solution of 3,7 dimethyloctyl 4-aminobenzoate (50% in diethyl phthalate, 0.4 g), 2 methyl butyraldehyde (0.2 g) in ethanol (1.4 g) was allowed to stand at ambient temperature for 3 hours. GC analysis showed the ratio of the aminobenzoate to the aldehyde complex as 15:85.

A solution of 3,7 dimethyloctyl 4-aminobenzoate (50% in diethyl phthalate, 0.2 g), 2 methyl butyraldehyde (0.1 g) in ethanol (0.6 g) and water (0.1 g) (equivalent to 15% aqueous ethanol) was allowed to stand at ambient temperature for 3 hours. GC analysis showed the ratio of hyde complex as 43:57.

A solution of 3,7 dimethyloctyl 4-aminobenzoate (50% in diethyl phthalate, 0.2 g), 2 methyl butyraldehyde (0.1 g) in ethanol (0.5 g) and water (0.2 g) (equivalent to 30% aqueous ethanol) was allowed to stand at ambient temperature for 3 hours. GC analysis showed the ratio of the aminobenzoate to the aldehyde complex as 67:33.

Figure 9:
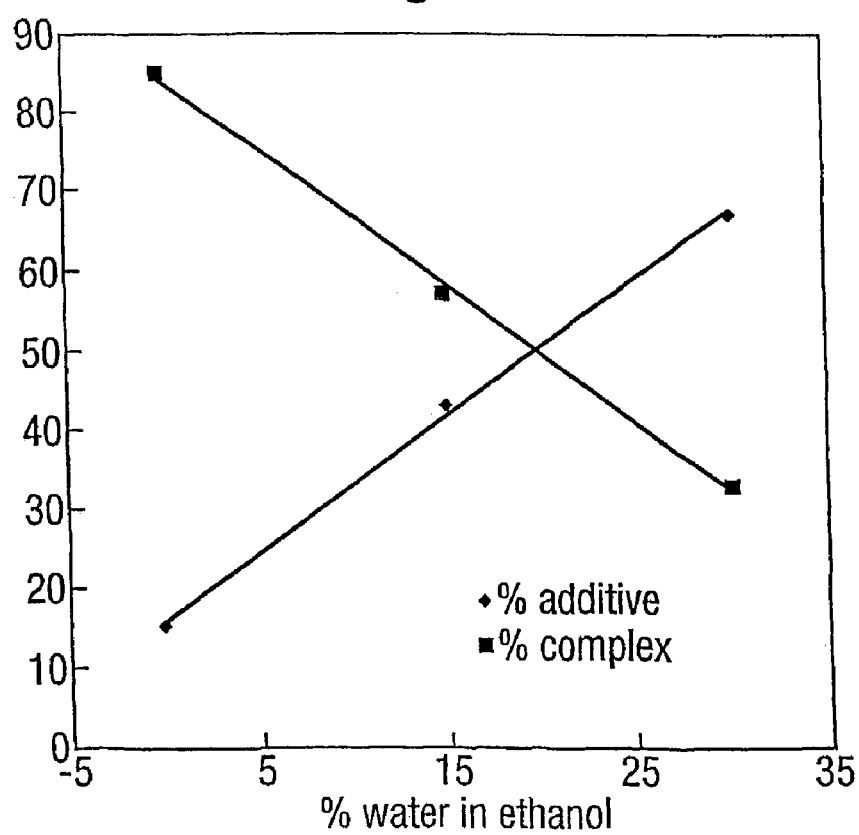
FIG. 9 is a graph of complex formation versus % water in ethanol for Example 7.

The results are tabulated below and are plotted in FIG. 9.

| % water | % additive | % complex |
|---|---|---|
| 0 | 15 | 85 |
| 15 | 43 | 57 |
| 30 | 67 | 33 |

From the graphical representation it can be seen that as the proportion of water in the solution is increased the proportion of the complex decreases, confirming the transient nature of the aldehyde complex formed 'in situ'.

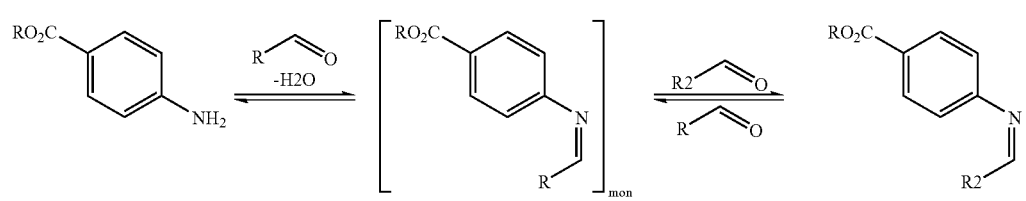

EXAMPLE 8

Equilibration of the Aldelydes

A solution of 3,7 dimethyloctyl 4-aminobenzoate (50% in diethyl phthalate, 0.4 g), 2 methyl butyraldehyde (0.2 g) in ethanol (1.4 g) was allowed to stand at ambient temperature for 3 hours. GC analysis showed the ratio of the aminobenzoate to the complex as 15:85. The addition of a second aldehyde (cyclohexane carboxaldehyde 0.1 g) gave the reduction in the 2-methyl butyraldehyde complex (M(+) 345) and the appearance of the corresponding cyclohexyl carboxaldehyde complex (M(+)371).

EXAMPLE 9

Additional Example of a Different Aminobenzoate Forming a Complex with an Aldehyde A solution of 3-methyl-5-phenylpentyl 4-aminobenzoate (50% in diethyl phthalate, 0.2 g), 2 methyl butyraldehyde (0.1 g) in ethanol (0.7 g) was allowed to stand at ambient temperature for 3 hours. GC analysis showed the ratio of the aminobenzoate to the complex as 25:75. Complex M(+) 365.

The invention claimed is:

1. A method of modifying a perfume composition or perfumed product, comprising adding to the perfume composition or perfumed product a substantially odourless aromatic amine trapping agent that chemically reacts spontaneously and reversibly in situ with a perfume in the composition or product to form a reaction product from which the perfume can be released from said composition or product, wherein the trapping agent comprises one or more of the following:
   3,7 dimethyloctyl 4-aminobenzoate
   3,5,5 trimethylhexyl 4-aminobenzoate
   2(E/Z)3,7 dimethyloct-2,6-dienyl 4-aminobenzoate
   3-methyl-5-phenylpentyl 4-aminobenzoate
   3,7,dimethyloct-6-enyl 4-aminobenzoate
   3[(4-aminobenzoyl)oxyl]-2 ethylhexyl 4-aminobenzoate.

2. A method according to claim 1, wherein the perfume includes a carbonyl group.

3. A method according to claim 2, wherein the perfume is an aldehyde or ketone.

4. A method according to claim 2 or 3, wherein the perfume and trapping agent react to form a Schiff's base reaction product.

5. A method according to claim 1, wherein the perfume is released from the reaction product by a hydrolysis reaction.

6. A method according to claim 1, wherein the reaction product is substantially odourless.

7. A method according to claim 1, wherein the composition further comprises one or more additional perfumes.

8. A method according to claim 1, wherein the composition further comprises solvent and/or solid substrate.

9. A method according to claim 1, wherein the composition comprises a perfume product.

* * * * *